(12) United States Patent
Leerkotte et al.

(10) Patent No.: US 10,545,127 B2
(45) Date of Patent: Jan. 28, 2020

(54) SENSOR AND METHOD FOR DETERMINING THE AIR RATIO OF A FUEL GAS/AIR MIXTURE

(71) Applicant: Elster GmbH, Mainz-Kastel (DE)

(72) Inventors: Bernardus Johannes Maria Leerkotte, Oldenzaal (NL); Christian Franz Hugo Schafer, Osnabruck (DE)

(73) Assignee: Elster GMBH, Mainz-Kastel (DE)

( * ) Notice: Subject to any disclaimer, the term of this patent is extended or adjusted under 35 U.S.C. 154(b) by 276 days.

(21) Appl. No.: 15/428,861

(22) Filed: Feb. 9, 2017

(65) Prior Publication Data
US 2017/0227514 A1 Aug. 10, 2017

(30) Foreign Application Priority Data
Feb. 9, 2016 (EP) ..................................... 16154849

(51) Int. Cl.
   G01N 33/22 (2006.01)
   G01N 21/71 (2006.01)
   G01N 21/75 (2006.01)

(52) U.S. Cl.
   CPC ........... *G01N 33/225* (2013.01); *G01N 21/71* (2013.01); *G01N 21/75* (2013.01); *G01N 2201/068* (2013.01)

(58) Field of Classification Search
   CPC ......... G01N 33/22; G01N 21/71; G01N 21/75
   USPC ...................... 422/54, 91; 436/143, 156, 171
   See application file for complete search history.

(56) References Cited

U.S. PATENT DOCUMENTS

| | | | | |
|---|---|---|---|---|
| 3,865,707 A | * | 2/1975 | Sayles | .................. G01N 27/407 204/410 |
| 3,955,921 A | * | 5/1976 | Tensmeyer | ................ A61L 2/14 422/22 |
| 3,960,495 A | * | 6/1976 | Tantram | .................. G01N 27/16 436/141 |
| 4,220,452 A | * | 9/1980 | Bray | ....................... G01N 25/50 436/156 |

(Continued)

FOREIGN PATENT DOCUMENTS

| | | |
|---|---|---|
| CN | 104823041 A | 8/2015 |
| DE | 4121924 A1 | 2/1992 |

(Continued)

OTHER PUBLICATIONS

The European Search Report for EP Application No. 16154849.0, dated Aug. 10, 2016.

*Primary Examiner* — Arlen Soderquist
(74) *Attorney, Agent, or Firm* — Shumaker & Sieffert, P.A.

(57) ABSTRACT

A sensor for determining an air ratio of a fuel gas/air mixture, wherein a housing is formed, which delimitates a measuring space. The housing has on one side a diffusion passage for coupling with a fuel gas/air mixture flow, wherein the diffusion passage is formed by a gas-permeable separating agent. An electrically operated excitation element is arranged for energy supply into the measuring space in order to induce a chemical reaction of a fuel gas/air mixture in the measuring space. At least one optical detection device is directed into the measuring space with its detection area, wherein the at least one optical detection device detects the intensity of radiation from the reaction position in at least a first wavelength range and produces a signal being allocated to the detected intensity, from which the air ratio is inferable.

17 Claims, 2 Drawing Sheets

(56) References Cited

U.S. PATENT DOCUMENTS

| | | | | |
|---|---|---|---|---|
| 4,367,130 | A * | 1/1983 | Lemelson | B01J 3/08 204/157.42 |
| 4,500,207 | A * | 2/1985 | Maiden | G01N 21/3518 250/343 |
| 4,517,161 | A * | 5/1985 | Gravina | G01N 27/122 324/71.5 |
| 4,659,306 | A | 4/1987 | Altemark et al. | |
| 5,037,291 | A | 8/1991 | Clark | |
| 5,037,619 | A * | 8/1991 | Alagy | B01J 4/04 422/607 |
| 5,314,249 | A * | 5/1994 | Marui | G01J 5/60 374/128 |
| 5,599,179 | A * | 2/1997 | Lindner | F23N 1/02 431/12 |
| 5,789,256 | A * | 8/1998 | Marlow | B01J 19/002 422/91 |
| 5,820,260 | A * | 10/1998 | Vander Heyden | G01N 25/22 374/37 |
| 6,237,575 | B1 * | 5/2001 | Lampert | F02D 41/0042 123/516 |
| 6,346,420 | B1 * | 2/2002 | Miric | G01N 25/54 422/94 |
| 6,640,199 | B1 * | 10/2003 | Goldstein | G01K 11/30 374/E11.014 |
| 9,829,455 | B2 * | 11/2017 | Watanabe | G01N 27/16 |
| 2003/0003590 | A1 | 1/2003 | Abbasi et al. | |
| 2003/0196458 | A1 * | 10/2003 | Bennett | C03B 37/04 65/377 |
| 2005/0208672 | A1 * | 9/2005 | Rue | G01N 21/76 436/143 |
| 2006/0234387 | A1 * | 10/2006 | Schaeffer | G01N 25/28 436/143 |
| 2008/0299505 | A1 * | 12/2008 | Winklhofer | F02D 35/022 431/79 |
| 2012/0154813 | A1 * | 6/2012 | Li | G01N 21/3504 356/437 |
| 2013/0340502 | A1 * | 12/2013 | Maruta | G01N 33/28 73/35.02 |
| 2015/0153294 | A1 * | 6/2015 | Watanabe | G01N 27/16 73/25.03 |
| 2016/0348901 | A1 * | 12/2016 | Karkow | F23D 1/00 |

FOREIGN PATENT DOCUMENTS

| | | |
|---|---|---|
| EP | 0156200 A1 | 10/1985 |
| EP | 1591723 A2 | 11/2005 |
| FR | 2816056 A1 | 5/2002 |
| JP | 1-237435 * | 9/1989 |
| WO | 2015054323 A1 | 4/2015 |

* cited by examiner

SENSOR AND METHOD FOR DETERMINING THE AIR RATIO OF A FUEL GAS/AIR MIXTURE

This application claims priority to European priority application No. 16154849.0 (EP 16 15 4849), filed on Feb. 9, 2016, entitled "Sensor And Method For Determining the Air Ratio of a Fuel Gas/Air Mixture", which is incorporated herein by reference.

BACKGROUND

The invention relates to a sensor for determining the air ratio of a fuel gas/air mixture and an associated method.

The measurement of the air ratio is extremely important in many combustion procedures, specifically to enable efficient and low-pollutant combustion processes to occur. In the field of automotive engineering, so-called Lambda ($\lambda$) sensors are known in this context, which are based mainly on the principle of electrochemical measuring cells. An example for such a sensor can be seen in WO 2009 144051 A1.

For changes in the mixture ratio and for changes in the size of the mass flow, such systems are limited in terms of their reaction time and their mass flow-dependent dead time and are also frequently very expensive to produce.

SUMMARY

The object of the invention is to provide a detection of the air ratio with favourable costs, rapid reaction time and short dead time.

The sensor as per the invention and the method as per the invention employ an optical measuring procedure for detecting the air ratio. A restricted measuring space is thereto formed, into which a fuel gas/air mixture can diffuse. According to the invention, a small proportion of an on-flowing fuel gas/air mixture is diverted, whereof in turn a small proportion participates in a controlled reaction. This reaction is optically monitored and the optical signals are evaluated.

The measuring space of the sensor, into which the fuel gas/air mixture diffuses for reaction and measurement, is restricted by a housing, wherein a permeable inlet to an on-flowing fuel gas/air mixture is provided. For example, a sensor as per the invention can be arranged in a gas condensing unit behind the mixing area, wherein the permeable inlet borders onto the flow path of the fuel gas/air mixture.

The diffusion passage can be variably designed, wherein the rapid mass exchange with the on-flowing fuel gas/air mixture should be guaranteed. On the other hand, the diffusion passage serves as a flame arrester, as chemical reactions take place in the measuring space and a flame separation from the on-flowing fuel gas/air mixture is required, even if there is no flame formation in the measuring space during proper operation. Accordingly, separating agents are formed in the diffusion passage with a suitability as flame arresters and are formed for example in the shape of a grid or metallic or ceramic grid or even as a sintered insert or frit.

A transfer of mass between the measuring space in the housing and the fuel gas/air mixture flowing on the other side of the separating agent takes place at any time by means of diffusion processes. The diffusion openings in the separating agent are thereby selected to be so small that turbulences in the on-flowing fuel gas/air mixture are not transferred into the measuring chamber.

An electrically operated excitation means is arranged within the measuring space. In this context, an electrically operated excitation means is understood to be any device that can effect an energy supply (or energy input) into the measuring space in order to induce a chemical reaction of a fuel gas/air mixture in the measuring space. Accordingly, the electrically operated excitation means can be a heating medium or ignition product. In any case, energy is purposefully introduced into the measuring space by the excitation means. The excitation means are positioned and organized in or at the measuring space such that the energy input is effected on a reaction position being located in the measuring space. This reaction position is formed in the measuring space within a quenching distance to the housing and/or separating layer. The distance to solid masses (e.g. walls of the housing) within which no flame formation can be maintained is described as the quenching distance. The solid masses absorb heat and also deflect this and effect an abortion of the reaction chain. The quenching distance is specifically dependent on the pressure of the mixture, the temperature of the walls of the cooling housing and the ratio of fuel and air, and therefore also the air ratio. Technical literature relating to the quenching distance is hereby referred to, e.g. "Verbrennung and Feuerungen", R. Günther, Springer-Verlag 2013. The quenching distance of a stoichiometric methane/air mixture at normal pressure is, for example, about 2 mm and for propane 1.8 mm.

The invention is based on the insight that an uncontrolled ignition with subsequent chain reaction in the measuring space is inhibited with such a design and dimensioning of a sensor. Nevertheless, it is evident that exothermic chemical reaction processes in the form of a combustion can be provoked in the immediate proximity of the energy input, specifically at the reaction position. According to the invention, the energy supply into the measuring space is controllable, as there is an electrically operated excitation means, which introduces different amounts of energy into the measuring space depending on the provided electrical energy. A chemical process is started at the position or in the area of the measuring space, into which energy is introduced. Precursors of an uncontrolled ignition are thereby specifically used. It has been shown that a formation of radicals occurs in the case of excitation of hydrocarbons (for example methane) by the excitation means. These reactive components, the number of which is dependent on the strength of the excitation, i.e. of the energy supply, can then react exothermically with a small amount of the oxygen being present in the measuring space depending on the air ratio. In the proximity of the reaction position, a type of ignition germ is thereby formed, which however cannot lead to an uncontrolled expansion of the chemical reaction processes in view of the dimensioning and position of the reaction position within the quenching distance to the proximity. The course of the chemical reaction processes is in fact limited to the proximity of the reaction position. The energy input should be regulated during operation such that a severely restricted reaction rate is spatially implemented. The reaction is a type of controlled sample combustion and leads to an emission of electromagnetic radiation as part of the exothermic reaction process when being realised with part of the oxygen in the measuring space. This emitted radiation is measured as per the invention by an optical detection device, the detection area of which in the measuring space is aimed at the reaction position. The optical detection device monitors the intensity of radiation around at least a first wavelength and produces from the detected radiation intensity at least one signal, from which the air ratio is inferable.

The invention uses the effect that the emission of IR, UV and visible light (or also radiation generation) of the reaction varies with the energy input by the excitation means depending on the air ratio. The exothermic reaction processes and also the expansion of the reaction zone are dependent on the air ratio. This effect is used in the sensor as per the invention to infer the air ratio from the radiation intensity around at least a first wavelength. The detection thereby can occur in a narrow or wide wavelength range around a central wavelength for example in an area of a known excitation level of involved molecules, specifically in the area of a known excitation level of water, which is formed during the combustion.

The intensity of the emitted radiation of the reaction varies with the air ratio. The reaction rate is higher if the reactive substances exist in the right mixing ratio. This can, for example, be the case if the air ratio ($\lambda$) is about equal to 1. With the optimal ratio, the expansion of the reaction zone develops maximally and/or the density of the reaction processes in the reaction zone is maximal. The radiation intensity around the excitation means is thereby also maximal. Accordingly, it can be detected by the optical detection devices and used to set the air ratio, for example by varying the mixing ratio until the intensity signal is maximal. This point can be used to calibrate the sensor.

Thus the described process uses a measuring space with excitation means, which through the input of energy induce chemical reaction processes at the reaction position in the fuel gas/air mixture without facilitating an explosive reaction process. The radiation of this chemical reaction is measured by an optical detection device and the radiation intensity is evaluated to determine the air ratio.

The reaction products are diffused after the reaction through the same diffusion passage in the measuring space into the flow of the fuel gas/air mixture, through which molecules of the fuel gas/air mixture are previously diffused into. New fuel gas/air mixture is diffused in the opposite direction. The measuring space requires no exhaust system or exhaust outlet, instead, the extremely low quantities of combustion products are conducted through the diffusion passage of the separating agent into the measuring gas flow. Nevertheless, discharge of gases from the measuring space through a separate outlet is generally also possible as part of the invention.

The energy supply is adapted subject to the selected fuel gas. An excessively strong energy supply leads indeed as applicable to chemical reaction processes in such a large area that the chemical reaction is saturated. In fact, as per the invention the optically measured reaction is initially started and the radiation intensity of the reaction zone is increased by increasing the energy supply in the measuring space, such an increase can lead to a saturation of the reaction process with an increase of the energy supply due to an excessively slow diffusion away of the waste gases from the reaction position. For diffused-in fuel gas and oxygen molecules, the probability of a reaction between radicals of the fuel gas and the oxygen then decreases as there are still reaction products in the reaction position, hampering the admittance of fuel gas molecules. Accordingly, an operating point can be selected, at which the energy supply is recorded and the diffusion processes enable a continual operation of the reaction. With such an operating point, the radiation intensity varies with the air ratio at a constant power supply and the sensor as per the invention and the method as per the invention can be used to determine the air ratio and regulate a mixture.

The sensor as per the invention can alternatively also be used in a regular operation, during which the radiation intensity of the reaction is kept constant through regulation by controlling the electrical power. The radiation intensity is then kept at a fixed setpoint in a certain air ratio range and the necessary electrical power is measured and used to determine the air ratio.

In a preferred embodiment, a measuring device for determining the electrical power is formed by the excitation means in the measuring space. With such a measuring device, there is at all times control and the possibility to regulate the supplied power.

Alternatively, a monitoring of the excitation means through independent measuring devices, specifically optical measuring devices, for example in the form of contactless temperature measuring devices, can be used.

The measured values of a power input can be used to control and calibrate the measuring device parts. Specifically, to record a calibration curve, the supplied power can be recorded together with the optical intensity signal of the monitored reaction in order to find an optimal operating point.

In a preferred embodiment of the invention, the excitation means are formed as an electrical heating device with ohmic heating. A current-carrying heating element is thereby provided, which is arranged within the measuring space at the reaction position. The excitation means has furthermore a controllable current or voltage source to supply this heating element.

The design of the sensor device and the execution of the method with an ohmic heater are an extremely cost-effective way to build the sensor. In addition, for heating devices with ohmic heaters, there is extensive prior art on the stable design of such heating devices. Heating wires or heating coils are easily available on the market. For example, such heating devices can be formed from high-temperature resistant metal alloys, which cope with the necessary thermal strain over a long period of time.

The ohmic heater is for example guided through two or also a plurality of contact points in the measuring space and brought to a desired temperature there by a current or voltage regulator. The radiation of the ohmic heating device can thereby be optically monitored to determine and adjust the temperature according to the principle of a pyrometer or contactless thermometer. The heat, which the heating element provides, stimulates the surrounding gas mixture in the measuring space. Accordingly, the immediate proximity along the heating element is the reaction position in this case. The energy supply occurs in this case using heat. An excitation of the gas mixture, a start and the maintenance of reaction processes of the produced radicals in the direct proximity of the heating element occur.

However, the optical effect of the heated heating element in its radiation is thereby preferably clearly displaced through filtration of the selected wavelength range in comparison to the wavelength, which is inferred with the optical detection device for deriving the air ratio.

Alternatively, two optical detection devices can be used, wherein one of these is selective for the radiation of the monitored reaction and the second optical detection device besides the intensity signal of the monitored reaction also measures the visible light radiation of the heating element. The differential signal of the detection devices is then used to calculate the temperature of the heating element. Accordingly, the emission by the heating element can be reliably measured.

The optical detection device can be equipped with filters to select the wavelengths to be monitored. The detection device for the reaction radiation detects for example a radiation emission of an excitation level of water in the wavelength range of 900 nm to 1100 nm. At the same time, a disruptive influence of the IR radiation of the heating element is also detected. The influence of this IR radiation can be compensated using the signal of the detected radiation of the heating element in the visible spectrum, whereby the reaction radiation is measured virtually independently of the infrared emission of the heating element.

An appropriately constructed sensor is cost-effective in production, long-lasting and indiscriminate in terms of applied voltages.

In an alternative embodiment of the invention, the excitation means comprises a number of constructively and galvanically separated electrodes. These extend at least partially into the measuring space and the excitation means has a power supply, which can generate a voltage, specifically also apply a high voltage at the electrodes. This embodiment serves to construct an energy-rich electrical field between the electrodes, such that reactions are stimulated therein. In a modification of this embodiment, ignition sparks can be produced by high voltage impulses, which allow a corresponding energy supply in this area.

In a further embodiment, a laser source is provided as a component of the excitation means, which radiates to the reaction position. Highly intensive laser light of a suitable wavelength (for example UV radiation), which is selected specifically at an excitation level of a fuel, can serve to supply energy to the reaction position.

In a particularly preferred and simple design, the optical detection device is formed with an optically sensitive means in the form of a photodiode, a phototransistor, a photo resistor or also a photodiode array. All these components are available and applicable in the standard market practice.

It is preferable when the optically sensitive means are provided with optical filters for the selection of a wavelength range.

As already described above, radiation can be produced by the excitation means itself, which is basically also measurable by the optical detection devices. This applies specifically to infrared and visible light radiation of heating elements, but also to high voltage flashes and laser pulses. The restriction of the detected wavelength spectrum by an optical filter on the optical detection device supplies a better signal-to-noise ratio and inhibits the detection of radiation, which is not caused by chemical reaction processes. The radiation intensity of the chemical reaction and that of the heating element can be separated by comparing the signals of two or a plurality of optical detection devices with different wavelength sensitivities.

It is further preferable that the gas-permeable separating agent, which forms the diffusion passage, is formed as a sintered pane or as a grid.

The separating agent also has besides the effect as a diffusion passage an effect as flame arrester, and also avoids the transmission of turbulences in the measuring space and the penetration of foreign bodies. The separating agent is to be produced from heat-resistant and non-combustible material.

It is further preferable when the excitation means is coupled with a controller to regulate the energy supply into the measuring space. The regulation can be effected thereby depending on the signal of the optical detection device.

The regulation of the energy supply to the excitation means can react to the radiation intensity detected by the optical detection device. This is specifically practical if no or only a low radiation intensity is detected, i.e. no detectable chemical reaction takes place. In this case, the power supply can be increased through the excitation means. In addition, an optimal operating point can be reached subject to the measured radiation intensity. It has been shown that when starting the sensor and with an increase of the power supply an exothermic chemical reaction is initially started in a small area, wherein this area and the chemical reaction rate enlarge with a further increase of the power supply. Depending on the available fuel gas/air mixture and the size of the measuring space together with the other constructive properties of the sensor, the enlargement of the firing range only occurs up to a limit, at the exceedance of which the speed of the mass transport of fuel to the excitation means and the removal of reaction products via the diffusion passage become a definitive size. In this area, an increase of the power supply no longer leads to an increase of the chemical reaction rate; it can instead lead to a partial or complete collapse of the reaction and an oscillating reaction process or a pulsating, repeated restart of the reaction processes after a partial compensation of the mass ratios through the diffusion processes. The construction of the sensor can also be such that the mass exchange via the diffusion passage is so large that the heating element due to its limited size cannot convert more fuel gas/air mixture by means of chemical reactions than can be supplied via the diffusion passage, even at raised temperatures. With such a construction of the sensor, saturation of the chemical reaction in the reaction position can occur because the reaction products cannot be sufficiently quickly discharged from the reaction position and therefore the replenishment of fuel gas and oxygen molecules is limited.

If a continual reaction is required, an adjustment of the power supply can be carried out at the excitation means depending on the measured optical signal.

In a further embodiment of the invention, it is preferable if the measuring device to capture the power supply has an optical sensor, which monitors the excitation means in the measuring space.

As described above, for example, a heating device can be monitored according to the principle of a pyrometer. This can also be done with a photodiode, which measures the emission of a heated filament or heating element being filtered into a spectral area. A measure for the current temperature can be derived from the signal of the photodiode.

The method as per the invention preferably uses the described sensor device. In any case, the method comprises the step of coupling a measuring space with a fuel gas/air mixture to be monitored, wherein the gas-permeable separating agent forming the diffusion passage is formed between the measuring space and the gas flow. The fuel gas/air mixture being located in the measuring space is then stimulated with the electrically operated excitation means in order to purposefully cause chemical reaction processes of the fuel gas/air mixture being diffused from the gas flow. This chemical reaction is optically measured, wherein the optical detection device in the measuring space is directed on at least one area of the reaction position and measures at least one spectral area of the excitation level of at least one reaction product. This spectral area comprises for example as a central wavelength an expected radiation transition of the reaction products. Specifically, exothermic chemical reactions can be measured here which lead to light emission due to the vibration and rotation level of the water molecule in the reaction zone. For example, the wavelength range of about 900 nm to 1100 nm, which is characteristic of an excitation mode of the water molecule can be monitored.

The chemical reaction is executed such in the measuring space that an explosive or uncontrolled exothermic chemical reaction cannot occur at any time. This is achieved by introducing the excitation energy for the provoked chemical reaction at a position in the measuring space, which is arranged within the quenching distance to the environment, i.e. specifically to the housing walls. In this way, the energy is only supplied to the measuring space in direct proximity to the excitation means, for example by means of a heating element in the form of a straight or shaped heating wire. An exothermic chemical reaction therefore takes place, wherein however no major flame formation occurs, but the reaction processes of the produced radicals within the quenching distance are maintained by continual external energy supply. If the supplied energy were disconnected, the reaction would end immediately, as the reaction maintenance is dependent on the external energy supply. In addition, the heating wire due to its temperature forms a flame arrester, whose quenching distance enlarges when the temperature drops. Nevertheless, the air ratio factor is inferable from the reaction.

The invention will now be explained in more detail on the basis of the attached figures.

DESCRIPTION

Figure 1:
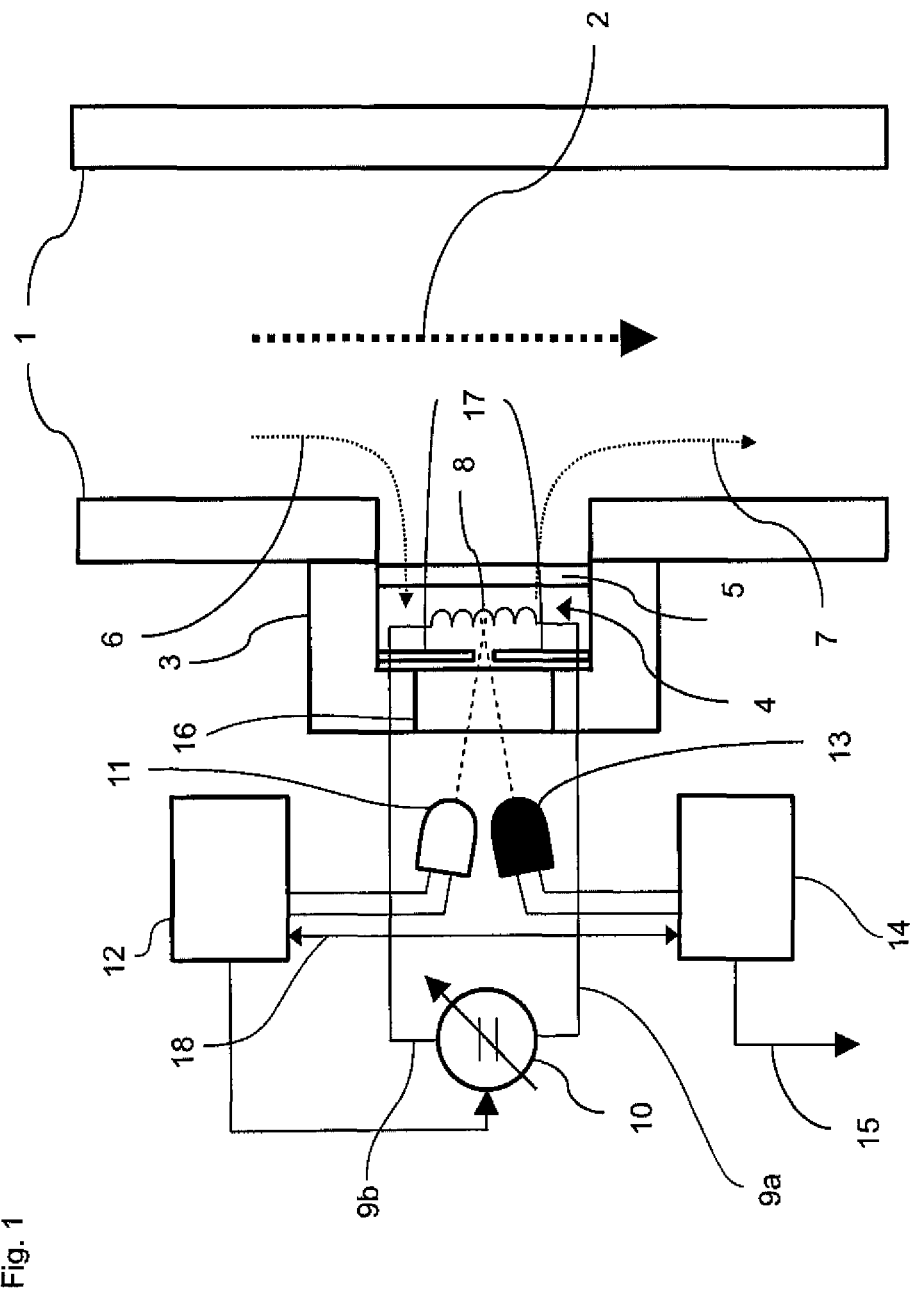
FIG. 1 shows the schematic structure of an embodiment of the invention.

In FIG. 1, a supply line 1 for a fuel gas/air mixture is shown. Along this supply line, the fuel gas/air mixture is supplied in the direction of the arrow 2 to a consumer, for example a heating burner. In an opening of the line 1, a sensor housing 3 is coupled gas-tightly with the line 1. The sensor housing 3 comprises a cavity 4, which is constructively separated from the gas flow 2 by a sintered pane 5. The sintered pane 5 provides as a separating agent for flame arrester and suppression of possible turbulence. The sintered pane 5 is permeable for the gas, such that portions of the fuel gas/air mixture can diffuse into the measuring space 4 according to arrow 6 at any time from the gas flow 2. In the same way, the substances can enter the gas flow 2 from the space 4 along the direction of the arrow 7.

In the measuring space 4, a heating wire 8 is arranged in the form of a heating coil. The line routings 9a, 9b to the heating wire 8 are gas-tightly fed through the housing 3 and coupled with a controllable voltage source 10. The heating wire 8 is heated subject to the set voltage at the voltage source 10.

In this embodiment, two photodiodes 11, 13 are arranged outside the measuring space. The measuring space comprises on its side facing the photodiodes 11, 13 a window 16, through which radiation from the measuring space 4 reaches the photodiodes 11, 13. Between the window 16 and the heating wire 8, a diaphragm 17 is arranged, which restricts the visual range of the photodiodes 11, 13 to a section of the heating wire 17.

The photodiode 11 is adjusted with its spectral sensitivity to the wavelength range of the visible light. It thereby measures the light emission of the aforementioned spectrum of the heating coil 8. The photodiode 11 is coupled with an evaluation circuit 12, which processes the signals of the photodiode. By means of the measurement of the emitted radiation, a measurement for the temperature of the heating coil 8 is determined and the evaluation circuit 12 can control the voltage source 10 in order to approximate the measured dimension for the actual temperature, calculated from the signals of the photodiode 11, to the fixed setpoint.

A further evaluation circuit 14 is coupled with the photodiode 13. The photodiode 13 is selected in this embodiment to detect electromagnetic radiation of reaction products in the area of the heating coil 8. In this embodiment, there is a photodiode, whose sensitivity range is especially high in the wavelength range of 800 nm to 1100 nm.

The evaluation circuit 12 and the evaluation circuit 14 are coupled via the connection 18. Data can be exchanged between the evaluation circuits via this connection (in practice, the evaluation circuits 12 and 14 can also be merged into one circuit).

The signal of this photodiode 13 is converted by the evaluation circuit 14 to supply a measuring signal 15. This measuring signal 15 is used in this embodiment to calculate the current air ratio on the basis of the calibration data.

With the depicted embodiment of the invention, a rapid and reliable determination of the air ratio of the on-flowing fuel gas/air mixture 2 is possible. If a fuel gas/air mixture passes the measuring space 4 along the arrow direction 2, a part of this fuel gas/air mixture diffuses into the measuring space 4 at all times by the diffusion processes. A small proportion of the molecules of the fuel gas/air mixture comes into contact with the heating wire 8 there. A significant aspect of the invention consists of the exothermic chemical reaction of a small proportion of the fuel gas/air mixture taking place in the measuring space 4 under controlled and safe conditions. As the heating wire 8 is located within the quenching distance of the surrounding walls and the sintered pane 5 also forms a flame arrester, this controlled exothermic chemical reaction is safe at all times. The exothermic chemical reaction in the direct proximity of the heating wire 8 is only maintained as energy is continually supplied via the voltage source 10. A self-sustaining combustion in the measuring space 4 is not possible due to the arrangement of the heating wire within the quenching distance. That a stimulated exothermic chemical reaction still occurs in direct proximity to the heating wire 8 is due to the continually supplied energy. In this way, the optical measurement of the chemical reaction and specifically the detection of the intensity of the emitted radiation has been made possible. The optical detection by the photodiode 13 is thereby adapted by an optical filter such to the chemical reaction that the characteristic excitation levels of the reaction products are measured during the chemical reaction processes. In this embodiment, an emission of a vibration-rotation excitation of water is measured in the range of 1000 nm as a characteristic wavelength. The spectral sensitivity of the photodiode 13 is selected accordingly.

The sensor as per the invention and the method as per the invention aim therefore to achieve an exothermic chemical sample reaction of the on-flowing fuel gas/air mixture, wherein this exothermic chemical sample reaction cannot lead to ignition of the fuel gas/air mixture of the supply gas flow 2.

The observations during measurements with the structure of the stated embodiment show with a fuel gas consisting primarily of methane that heat is initially discharged through the gas mixture to the walls 3 when starting the device and during an initial heating of the heating coil 8. With an increase of heating temperature of the heating wire 8, monitored by the photodiode 11, exothermic chemical reaction processes occur on the surface of the heating wire 8. This is measured at least by the photodiode 13. A thin reaction layer thereby initially forms over the heating wire 8, whose light intensity further increases in the monitored wavelength range of 1000 nm with temperature increase. The thickness of the reaction layer and the density of the occurring reaction processes in the reaction position around the heating wire 8 increase thereby with a rising temperature.

If the mass transfer of fuel gas and oxygen molecules via the diffusion passage is lower than the rate of the molecules reacting at the heating wire, a substantial reaction collapse and a subsequent upsurge of the radiation intensity (dependent on the air ratio) ultimately occurs with a further increase of the temperature. A type of pulsating of the light intensity therefore occurs. If however sufficient fuel gas and oxygen molecules are supplied via the diffusion passage for the exothermic chemical reaction processes, such quantities of reaction products are released with an increasing temperature that these surround the heating wire and limit the arriving current of fuel gas and oxygen molecules. A saturation of the exothermic chemical reactions occurs. This then leads to the radiation intensity of the chemical reaction being saturated.

Accordingly, the temperature of the heating wire 8 is selected such that a continual, non-oscillating and non-saturated chemical reaction is observed on the surface of the heating wire 8. An oscillating or saturated operation can thereby initially be started, for example, and the temperature can then be reduced. The evaluation of the emission in non-oscillating operation is in this example the preferred variation, however the oscillating operation can also be used for an evaluation.

Figure 2:
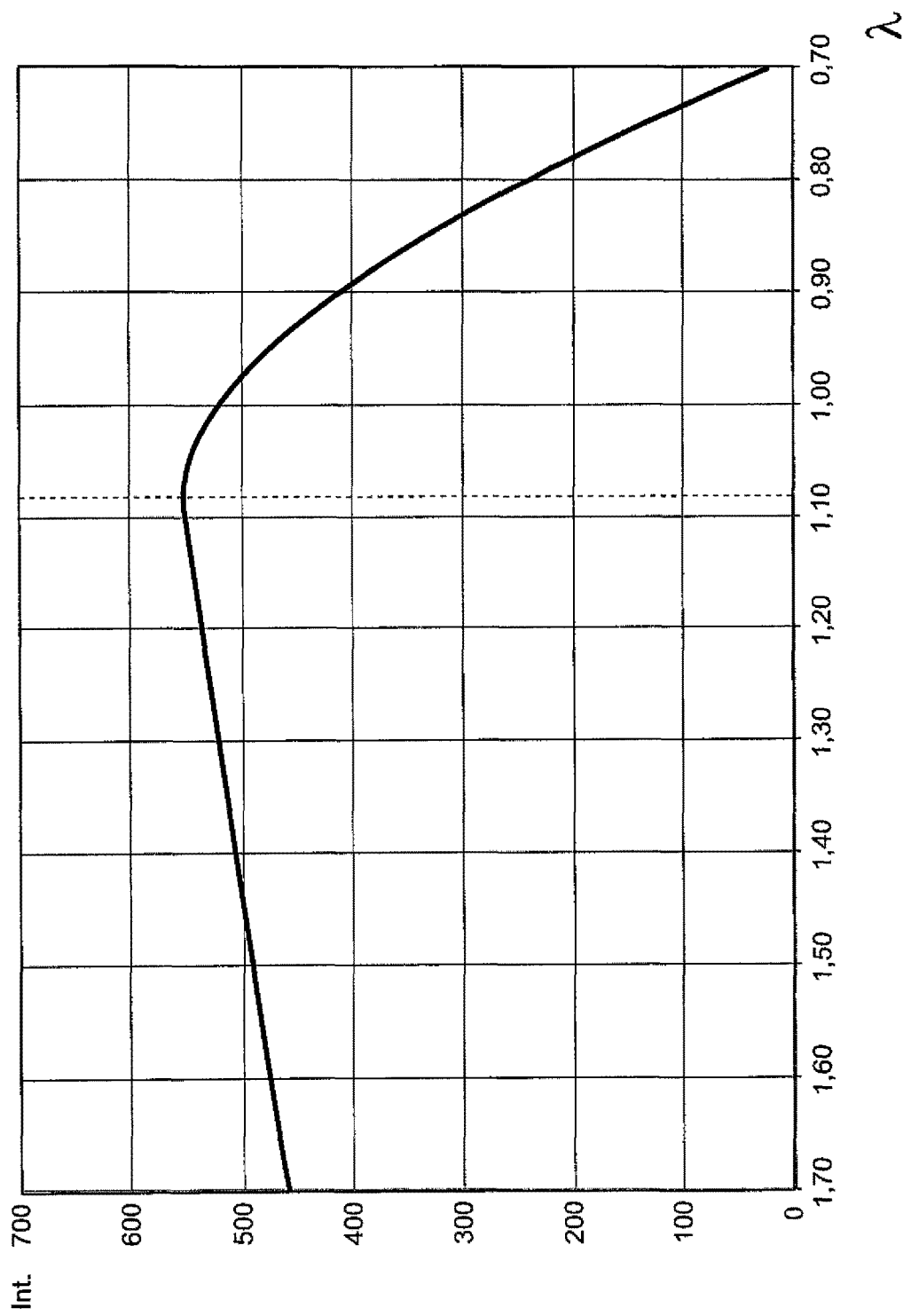
FIG. 2 shows an example of a radiation intensity curve depending on the air ratio.

In FIG. 2, a course of measurement of the sensor device as per the invention is shown as per the embodiment. The data is produced from averaged measurement data and extends over a measuring range of the air ratio of $\lambda=0.70$ to $\lambda=1.70$. The air ratio was thereby calculated in the gas flow by a conventional gas analysis device. The scaling of the intensity axis (Y-axis) has been selected for a qualitative representation of the measurement values.

The above described curve progression therefore occurs with a virtually linear course of measurement for lean mixtures and a steep drop to increasingly rich mixtures.

The linear increase of the intensity with an air ratio change of 1.70 to 1.10 can be explained thus that there is less and less excess air and this is why the temperature of the reaction layer increases around the heating wire. This leads to the forming of more radicals and the reaction layer around the heating wire expands and/or the density of the water-forming, exothermic chemical reaction processes increases, which leads to a higher light emission in the wavelength range around 1000 nm.

The maximum of the curve is near that of the stoichiometric mixture when using methane as the fuel gas, but not exactly $\lambda=1$, rather about $\lambda=1.07$. The curve moves towards the right with a propane-air mixture. The maximum is then at around $\lambda=0.9$ (depending on the heating wire temperature).

To carry out a calibration at $\lambda=1.0$, the sensor as per the invention offers a further possible use.

With a specific reduction of the temperature of the heating wire, the effective area of the sensor is in fact restricted. Especially in the range of $\lambda<=1$, the detectable reaction processes break down. This allows a fuel gas/air mixture to be provided through the interaction with the burner controller and a variation of the fuel gas/air ratios, which just enables reaction processes.

Thus, both the mixture ratio is repetitively varied and the temperature of the heating wire is repetitively reduced until a point is determined, which still permits a reaction with radiation emission, from which however a collapse of the reaction (disappearance of the radiation) occurs in each of the direction of both a leaner and richer mixture.

The thus determined fuel gas/air mixture has an air ratio of about $\lambda=1.0$, independent of the type of fuel gas.

After this point has been determined, the heating wire is increased back to a normal operating temperature while maintaining the thus adjusted fuel gas/air ratio. The size of the signal then corresponds to the value for an air ratio of $\lambda=1.0$.

There are thus two points, which can be determined characteristically for the burner operation on the basis of the measurements. The point of the aforementioned maximum of radiation intensity represents a fixed point depending on the type of gas. In addition, the sensor can be calibrated to the point $\lambda=1.0$.

The method as per the invention and also the sensor as per the invention could be adapted in many ways. For example, the sensor can be constructed in multiple pieces and it is basically also possible to provide a gas discharge on the sensor, instead of conducting the gas into the gas flow. The essential thing is that a part of the gas flow is diverted and that the emitted emission of a controlled exothermic chemical reaction is optically measured in order to determine the air ratio. Thereupon, an optimization of the fuel gas/air mixture can be carried out. An alternative with an optical measurement of a chemical sample reaction is thereby added to the known methods from prior art, during which electro-chemical effects are used substantially to determine the air ratio. Thereby the chemical sample reaction takes place at all times in a controlled manner and in such a dimensioned structure that no self-preserving or uncontrolled exothermic chemical reaction of the fuel gas/air mixture is possible in the measuring space.

What is claimed:

1. A sensor for determining an air ratio of a fuel gas/air mixture, the sensor comprising:
    a housing that delimitates a measuring space, and a diffusion passage that fluidly couples the measuring space with a fuel gas/air mixture flow, wherein the diffusion passage includes a gas-permeable separating member that spans between the fuel gas/air mixture flow and the measuring space;
    an electrically operated excitation element for supplying energy into the measuring space in order to induce a chemical reaction of a fuel gas/air mixture in the measuring space, wherein the excitation element is configured to supply energy to a reaction position located in the measuring space, wherein the reaction position is located within a quenching distance of the housing and/or the gas-permeable separating member;
    at least one optical detection device whose detection area is directed into the measuring space, wherein the at least one optical detection device is configured to detect an intensity of radiation from the reaction position in at least a first wavelength range and produces a signal that is indicative of the detected intensity, from which the air ratio is inferable; and a controller operatively coupled to the excitation element in order to regulate the energy supplied to the measuring space, wherein the energy that is supplied by the excitation element is regulated based at least in part on the signal of the at least one optical detection device.

2. The sensor according to claim 1, further comprising a measuring device to quantitatively capture an energy level supplied to the excitation element.

3. The sensor according to claim 1, wherein the excitation element comprises an electrical heating device with a current-carrying ohmic heating element, wherein the current-carrying ohmic heating element is arranged within the measuring space at the reaction position and wherein the heating element is supplied by a controllable current or voltage source.

4. The sensor according to claim 1, wherein the excitation element is formed with a plurality of constructively and galvanically separated electrodes, which extend at least in part into the measuring space, wherein the excitation element further comprises a power supply coupled with the electrodes, wherein the reaction position is located between the electrodes.

5. The sensor according to claim 1, wherein the excitation element comprises a laser light source, which radiates light into the measuring space at the reaction position.

6. The sensor according to claim 1, wherein the at least one optical detection device comprises an optically sensitive detector.

7. The sensor according to claim 6, wherein the at least one optical detection device comprises an optical filter for selecting the first wavelength range.

8. The sensor according to claim 1, further comprises an optical element arranged between the reaction position and the at least one optical detection device, the optical element configured to direct the radiation from a subsection of the reaction position to the optical detection device.

9. The sensor according to claim 8, wherein the optical element includes a diaphragm, a light conductor, or a lens.

10. The sensor according to claim 1, further comprising a measuring device configured to optically monitor the energy supplied by the excitation element to the measuring space.

11. A method for determining an air ratio of a fuel gas/air mixture, the method comprising:
fluidly coupling via a gas-permeable separating member a measuring space with a gas flow to be monitored, the gas flow having a fuel gas/air mixture;
exciting gases located in the measuring space with an electrically operated excitation element in order to induce a chemical reaction of a fuel gas/air mixture in the measuring space without inducing a flame in the measuring space;
monitoring the measuring space with an optical detection device in a predetermined spectral region, and detecting an intensity of an optical emission from the chemical reaction of the fuel gas/air mixture in the measuring space;
applying power to the electrically operated excitation element such that optical emission from the chemical reaction of the fuel gas/air mixture in the measuring space remains substantially at a predetermined value; and
calculating the air ratio of the fuel gas/air mixture based at least in part on the intensity of the optical emission.

12. The method according to claim 11, wherein the exciting step includes applying power to an ohmic heating element that is positioned in the measuring space.

13. The method according to one of claim 11, wherein the air ratio is changed and an applied power to the electrically operated excitation element is reduced until the chemical reaction in the measuring space is only just measurable with a single fuel gas/air mixture, in order to adjust an air ratio of the fuel gas/air mixture to a $\lambda=1.0$.

14. The method according to claim 11, wherein the predetermined spectral region comprises a wavelength of 1000 nm.

15. The method according to claim 11, wherein the predetermined spectral region comprises a wavelength range from 900 nm to 1100 nm.

16. A sensor for detecting an air ratio of a fuel gas/air mixture, the sensor comprising:
a body with a diffusion passage leading to a measuring space, the diffusion passage fluidly couplable to a fuel gas/air mixture flow;
an excitation element for supplying energy into the measuring space in order to induce a chemical reaction of a fuel gas/air mixture in the measuring space without inducing a flame in the measuring space;
an optical detection device configured to detect an intensity of an optical emission from the chemical reaction of the fuel gas/air mixture in the measuring space; and
a controller operatively coupled to the excitation element in order to regulate the energy supplied to the measuring space, wherein the energy that is supplied by the excitation element is regulated based at least in part on the optical emission intensity detected by the optical capturing device.

17. The sensor of claim 16, wherein the air ratio of the fuel gas/air mixture is based at least in part on the optical emission from the chemical reaction of the fuel gas/air mixture in the measuring space.

* * * * *